United States Patent
Tomaki et al.

(10) Patent No.: US 12,209,058 B2
(45) Date of Patent: Jan. 28, 2025

(54) METHOD FOR PRODUCING AROMATIC AMINOMETHYL

(71) Applicant: MITSUBISHI GAS CHEMICAL COMPANY, INC., Chiyoda-ku (JP)

(72) Inventors: Keisuke Tomaki, Okayama (JP); Shiori Shinagawa, Tokyo (JP); Shinyou Shirai, Okayama (JP)

(73) Assignee: MITSUBISHI GAS CHEMICAL COMPANY, INC., Chiyoda-ku (JP)

( * ) Notice: Subject to any disclaimer, the term of this patent is extended or adjusted under 35 U.S.C. 154(b) by 556 days.

(21) Appl. No.: 17/629,906

(22) PCT Filed: Jul. 22, 2020

(86) PCT No.: PCT/JP2020/028369
§ 371 (c)(1),
(2) Date: Jan. 25, 2022

(87) PCT Pub. No.: WO2021/020258
PCT Pub. Date: Feb. 4, 2021

(65) Prior Publication Data
US 2022/0251022 A1    Aug. 11, 2022

(30) Foreign Application Priority Data
Jul. 31, 2019  (JP) ................. 2019-141419

(51) Int. Cl.
*C07C 209/48* (2006.01)
*B01J 23/75* (2006.01)
*B01J 23/755* (2006.01)

(52) U.S. Cl.
CPC ............. *C07C 209/48* (2013.01); *B01J 23/75* (2013.01); *B01J 23/755* (2013.01)

(58) Field of Classification Search
None
See application file for complete search history.

(56) References Cited

U.S. PATENT DOCUMENTS

| 6,011,179 A | 1/2000 | Haas et al. |
| 6,455,724 B1 | 9/2002 | Ionkin |
| 2005/0101797 A1 | 5/2005 | Allgeier |

FOREIGN PATENT DOCUMENTS

| CN | 1523007 A | 8/2004 |
| JP | 54-41804 A | 4/1979 |
| JP | 11-222465 A | 8/1999 |
| JP | 2002-205980 A | 7/2002 |
| JP | 2002-322138 A | 11/2002 |
| JP | WO 03/029194 A1 | 4/2003 |
| JP | 2003-327563 A | 11/2003 |
| WO | WO 2022/019105 A1 | 1/2022 |

OTHER PUBLICATIONS

International Search Report mailed on Oct. 6, 2020 in PCT/JP2020/028369 filed on Jul. 22, 2020 (2 pages).
Gregg et al., "Doping Molecular Semiconductors: n-Type Doping of a Liquid Crystal Perylene Diimide", Journal of the American Chemical, Society, 2001, vol. 123, No. 32, 7 total pages.
Shen et al., "Synthesis of m-Xylylenediamine by Hydrogenation with Modified Raney-Ni Catalyst", Fine Chemicals, China Academic Journal Electronic Publishing House, Sep. 25, 2000, vol. 17, No. 9, pp. 544-546 (12 total pages, with unedited computer-generated English translation).

*Primary Examiner* — Sudhakar Katakam
*Assistant Examiner* — Jennifer C Sawyer
(74) *Attorney, Agent, or Firm* — Oblon, McClelland, Maier & Neustadt, L.L.P.

(57) ABSTRACT

A method for producing an aromatic aminomethyl, comprising hydrogenating an aromatic nitrile in a mixed solvent comprising a hydrocarbon solvent and a polar organic solvent having a solubility parameter (SP value) of 10 or more in the presence of a quaternary ammonium compound and a hydrogenation catalyst.

20 Claims, No Drawings

METHOD FOR PRODUCING AROMATIC AMINOMETHYL

CROSS-REFERENCE TO RELATED APPLICATIONS

The present application is a 35 U.S.C. § 371 national stage application of International patent application PCT/JP2020/028369, filed Jul. 22, 2020, which is based on and claims the benefit of priority to Japanese Application No. 2019-141419, filed Jul. 31, 2019. The entire contents of these applications are incorporated herein by reference.

TECHNICAL FIELD

The present invention relates to a method for producing an aromatic aminomethyl by hydrogenating an aromatic nitrile.

BACKGROUND ART

An aromatic aminomethyl is useful as a starting material or an intermediate for drugs, agricultural chemicals, resins, curing agents, etc. In particular, xylenediamine having two aminomethyl groups is a very useful compound as a starting material for a polyamide resin, a curing agent or the like, or an intermediate for an isocyanate.

As a method for producing an aromatic aminomethyl, a method in which an aromatic nitrile is hydrogenated is carried out.

In the hydrogenation of the aromatic nitrile, a technique using liquid ammonia as a solvent is known. From the environmental consideration, however, liquid ammonia needs to be recovered without releasing it to the outside after the hydrogenation reaction, so that the production load is heavy, and regarding a production method without using liquid ammonia, various studies have been made.

For example, in Patent Literature 1, a method in which a nitrile is hydrogenated in a mixed solvent of lower alcohols and cyclic hydrocarbons in the presence of a hydroxide or an alcoholate of an alkali or alkaline earth metal and a Raney nickel or Raney cobalt catalyst is disclosed for the purpose of obtaining primary amines including an aromatic aminomethyl in a high yield.

In Patent Literature 2, a method for producing an aromatic cyanoaminomethyl, in which an aromatic nitrile is hydrogenated using a palladium catalyst in the presence of an alcohol and a tetraalkylammonium hydroxide, is disclosed for the purpose of obtaining an aromatic cyanoaminomethyl that is one of aromatic aminomethyls in a high yield.

CITATION LIST

Patent Literature

PTL1: JP 54-41804 A
PTL2: JP 2002-205980 A

SUMMARY OF INVENTION

Technical Problem

In order to use an aromatic aminomethyl as a starting material for a polyamide resin, a curing agent or the like, or an intermediate for an isocyanate, an aromatic aminomethyl of extremely high purity has been desired, and in the production method without using liquid ammonia, a method for obtaining an aromatic aminomethyl in a high yield has been desired.

An attempt to obtain an aromatic aminomethyl by adding a base without using liquid ammonia as in Patent Literature 1 has been made, but a problem is that deterioration of a catalyst tends to proceed if an alkali metal or the like is used, resulting in decreased productivity.

On that account, a synthesis method that gives a high yield, inhibits deterioration of a catalyst and enhances productivity has been desired.

Then, an object of the present invention is to provide a production method by which an aromatic aminomethyl is obtained in a high yield without substantially using liquid ammonia, and deterioration of a catalyst can be inhibited.

Solution to Problem

The present inventors have earnestly studied, and as a result, they have found that the above object can be achieved by carrying out hydrogenation of an aromatic nitrile in a specific mixed solvent in the presence of a quaternary ammonium compound and a catalyst.

That is to say, the present invention is a method for producing an aromatic aminomethyl, comprising hydrogenating an aromatic nitrile in a mixed solvent comprising a hydrocarbon solvent and a polar organic solvent having a solubility parameter (SP value) of 10 or more in the presence of a quaternary ammonium compound and a hydrogenation catalyst.

Advantageous Effects of Invention

According to the production method of the present invention, an aromatic aminomethyl can be obtained in a high yield without substantially using liquid ammonia, and deterioration of a catalyst can also be inhibited.

DESCRIPTION OF EMBODIMENTS

The method for producing an aromatic aminomethyl of the present invention comprises hydrogenating an aromatic nitrile in a mixed solvent comprising a hydrocarbon solvent and a polar organic solvent having a solubility parameter (SP value) of 10 or more in the presence of a quaternary ammonium compound and a hydrogenation catalyst.

The production method of the present invention will be described in detail hereinafter.

(Hydrocarbon Solvent)

The hydrocarbon solvent used in the present invention is one or more selected from the group consisting of an aromatic hydrocarbon solvent and an aliphatic hydrocarbon solvent, and an aromatic hydrocarbon solvent is preferable.

The solubility parameter (also referred to as SP value hereinafter) of the hydrocarbon solvent is preferably 9.5 or less, and more preferably 9.0 or less. The lower limit value is preferably 7.0 or more, and more preferably 8.0 or more. It is thought that when the hydrocarbon solvent is an aromatic hydrocarbon solvent, an aromatic nitrile and hydrogen that are starting materials are favorably dissolved, and hydrogenation reaction can be efficiently carried out. It is thought that also due to the SP value of 9.5 or less, an aromatic nitrile and hydrogen that are starting materials are favorably dissolved, and hydrogenation reaction can be efficiently carried out.

When the hydrocarbon solvent is an aromatic hydrocarbon solvent, the number of carbon atoms of the aromatic hydrocarbon solvent is preferably 7 to 12, more preferably 7 to 9, and still more preferably 8 to 9.

Specific examples of the aromatic hydrocarbon solvents include monocyclic aromatic hydrocarbon compounds, such as toluene, ethylbenzene, three isomers of xylene (o-xylene, m-xylene, p-xylene), mesitylene and pseudocumene, and polycyclic aromatic hydrocarbon compounds, such as naphthalene and methylnaphthalene, and monocyclic aromatic hydrocarbon compounds are preferable, and from the viewpoint of industrially easy availability, xylene and mesitylene are more preferable, xylene (SP value 8.8) is still more preferable, m-xylene and p-xylene are still much more preferable, and m-xylene is still much more preferable.

(Polar Organic Solvent Having Solubility Parameter (SP Value) of 10 or More)

The polar organic solvent used in the present invention has a solubility parameter (SP value) of 10 or more, preferably 11 or more, more preferably 12 or more, and still more preferably 13 or more. The upper limit value is preferably 20 or less, more preferably 17 or less, and still more preferably 15 or less.

The SP value in the present invention is a value determined by the following Hildebrand solubility parameter equation.

$$\text{Solubility parameter (SP value)} = (\Delta H_A^V - RT)^{0.5}/V_A^{0.5}$$

$\Delta H_A^V$: enthalpy of vaporization of liquid A (polar organic solvent)
R: gas constant
T: temperature
$V_A$: molar volume of liquid A It is thought that by using a polar organic solvent having a SP value of 10 or more in the production method of the present invention, an aromatic aminomethyl that is a product distributes therein, and the hydrogenation reaction can be efficiently promoted.

The polar organic solvent used in the present invention is one or more selected from the group consisting of an alcohol, an ester, an amide, a sulfoxide, a ketone and an amine, and an alcohol is preferable.

Examples of the alcohols include a monohydric alcohol and a polyhydric alcohol, and a monohydric alcohol is preferable. Examples of the monohydric alcohols include an aliphatic alcohol and an aromatic alcohol, and an aliphatic alcohol is preferable.

From the viewpoint of industrially easy availability, the number of carbon atoms of the aliphatic alcohol is preferably 1 to 8, more preferably 1 to 4, and still more preferably 1 or 2.

Specific examples of the aliphatic alcohols include methanol (SP value 14.5), ethanol (SP value 12.7), n-propanol (SP value 11.9), isopropanol (SP value 11.5), n-butanol (SP value 11.4), sec-butanol (SP value 10.8), tert-butanol (SP value 10.6), pentanol, hexanol (SP value 10.7), heptanol (SP value 10.6), and n-octanol (SP value 10.3), and preferable are methanol and ethanol, and more preferable is methanol.

(Mixed Solvent)

The mixed solvent in the present invention refers to the whole of liquid compounds contained in the solution in the hydrogenation reaction, except an aromatic nitrile that is a starting material and an aromatic aminomethyl that is a product.

The mass ratio of the hydrocarbon solvent to the polar organic solvent (hydrocarbon solvent/polar organic solvent) in the mixed solvent is preferably 60/40 to 99/1, more preferably 70/30 to 99/1, still more preferably 80/20 to 99/1, and still much more preferably 82/18 to 99/1. By using the hydrocarbon solvent in a larger amount than that of the polar organic solvent, the concentration of the nitrile dissolved in the hydrocarbon solvent is decreased, and a high-boiling point substance is hardly formed on the catalyst.

The total content of the hydrocarbon solvent and the polar organic solvent in the mixed solvent is preferably 90 to 100 mass %, more preferably 95 to 100 mass %, and still more preferably 99 to 100 mass %.

The content of water in the mixed solvent is preferably 5 mass % or less, more preferably 2 mass % or less, and still more preferably 1 mass % or less. It is thought that by setting the water content to 5 mass % or less, side reaction with the starting material can be inhibited, and the yield of the product can be enhanced.

It is preferable that the mixed solvent in the present invention should not contain liquid ammonia. Since the liquid ammonia is not contained, the production load imposed on the recovery of ammonia can be reduced.

A difference in the SP value between the hydrocarbon solvent and the polar organic solvent in the mixed solvent is preferably 0.5 or more, more preferably 1.0 or more, still more preferably 2.0 or more, and still much more preferably 4.0 or more. The difference is preferably 12 or less, more preferably 10 or less, still more preferably 8 or less, and still much more preferably 6 or less.

A combination of the hydrocarbon solvent and the polar organic solvent in the mixed solvent is preferably that of a monocyclic aromatic hydrocarbon compound and an alcohol, more preferably that of xylene and an aliphatic alcohol having 1 or 2 carbon atoms, and still more preferably that of m-xylene and methanol.

(Quaternary Ammonium Compound)

Examples of the quaternary ammonium compounds used in the present invention include a tetraalkylammonium hydroxide and an organic acid tetraalkylammonium salt, and it is preferable to use one or more selected from the group consisting of these, and among these, a tetraalkylammonium hydroxide is more preferable.

Since the quaternary ammonium compound is not such a strong alkali as an alkali metal hydroxide, corrosion of a reaction container and the like, deterioration of a catalyst, etc. do not occur, and an aromatic aminomethyl can be stably obtained in a high yield.

Examples of the tetraalkylammonium hydroxides include tetramethylammonium hydroxide, tetraethylammonium hydroxide and tetrabutylammonium hydroxide, and preferable are tetramethylammonium hydroxide and tetraethylammonium hydroxide, and from the viewpoint of enhancing the yield and from the viewpoint of reducing impurities, tetraethylammonium hydroxide is more preferable, and from the viewpoint of availability, tetramethylammonium hydroxide is more preferable.

Examples of the organic acid tetraalkylammonium salts include a tetraalkylammonium phenoxide, a fatty acid tetraalkylammonium salt, and a tetraalkylammonium tetraphenylborate.

The fatty acid tetraalkylammonium salt is, for example, tetramethylammonium acetate.

The amount of the quaternary ammonium compound is preferably 0.1 to 10 mmol, more preferably 0.2 to 5 mmol, and still more preferably 0.5 to 1 mmol, based on 1 g of the hydrogenation catalyst. The amount thereof is preferably 1 to 20 mass %, more preferably 3 to 10 mass %, and still more preferably 5 to 10 mass %, based on the hydrogenation catalyst. By using the quaternary ammonium compound in the above amount, the catalyst is not deteriorated even when it is repeatedly used, the reaction rate is maintained, and a desired aromatic aminomethyl can be obtained in a high yield. When the amount of the quaternary ammonium compound is 20 mass % or less based on the hydrogenation catalyst, the amount of water brought into can be suppressed even if the quaternary ammonium compound is used as an aqueous solution.

(Hydrogenation Catalyst)

The hydrogenation catalyst used in the production method of the present invention is not restricted as long as it is a catalyst used for hydrogenation of an organic compound, but a metal catalyst is preferable, and examples of the metals include cobalt, nickel, palladium and platinum, and preferable is one or more selected from the group consisting of cobalt and nickel, and more preferable is cobalt. That is to say, a metal catalyst containing one or more selected from the group consisting of cobalt, nickel, palladium and platinum is preferable, a metal catalyst containing one or more selected from the group consisting of nickel and cobalt is more preferable, and a metal catalyst containing cobalt is still more preferable. By using a cobalt catalyst, formation of a high-boiling substance on the catalyst is inhibited, the yield can be enhanced, and moreover, deterioration of the catalyst can also be reduced.

Examples of the metal catalysts containing one or more selected from the group consisting of nickel and cobalt include a metal-supported catalyst and a sponge metal catalyst, and preferable is a sponge metal catalyst.

Examples of the metal-supported catalysts include catalysts in which one or more selected from the group consisting of nickel and cobalt are supported on $Al_2O_3$, $SiO_2$, diatomaceous earth, $SiO_2$—$Al_2O_3$, or $ZrO_2$ by a precipitation method.

Examples of the sponge metal catalysts include catalysts formed by eluting part of components from an alloy of two or more components (nickel, cobalt, aluminum, iron, copper, etc.) using an acid or an alkali, and preferable are a sponge cobalt catalyst and a sponge nickel catalyst, and more preferable is a sponge cobalt catalyst. The above catalysts may be used singly or in combination of two or more.

The amount of the catalyst is preferably 0.1 to 100 parts by mass, more preferably 1 to 50 parts by mass, and still more preferably 10 to 20 parts by mass, based on 100 parts by mass of the aromatic nitrile. By using the catalyst in the above amount, the yield of the resulting aromatic aminomethyl can be enhanced.

(Aromatic Nitrile)

The aromatic nitrile used as a starting material in the production method of the present invention is one in which a nitrile group is bonded to an aromatic ring (benzene ring), and the number of nitrile groups is preferably 1 or 2, and more preferably 2.

To the aromatic ring, other substituents may be bonded.

Specific examples of the aromatic nitriles include benzonitrile and dicyanobenzene, and dicyanobenzene is preferably used.

The dicyanobenzene has three isomers of phthalonitrile (1,2-dicyanobenzene), isophthalonitrile (1,3-dicyanobenzene), and terephthalonitrile (1,4-dicyanobenzene), and preferable are isophthalonitrile and terephthalonitrile, and more preferable is terephthalonitrile.

The concentration of the aromatic nitrile in the reaction solution in the hydrogenation reaction is preferably 2 to 30 mass %, more preferably 5 to 25 mass %, and still more preferably 7 to 20 mass %. In the reaction solution, a catalyst is not contained.

(Aromatic Aminomethyl)

The aromatic aminomethyl obtained by the production method of the present invention is one in which an aminomethyl group is bonded to an aromatic ring (benzene ring), and the number of aminomethyl groups is preferably 1 or 2, and more preferably 2.

To the aromatic ring, other substituents may be bonded.

Specific examples of the aromatic aminomethyls include benzylamine and xylenediamine, and preferable is xylenediamine.

The xylenediamine has three isomers of ortho-xylenediamine, meta-xylenediamine and para-xylenediamine, and preferable are meta-xylenediamine and para-xylenediamine, and more preferable is para-xylenediamine.

These isomers of the xylenediamine can be each obtained by the production method of the present invention using the corresponding dicyanobenzene as a starting material.

(Method for Producing Aromatic Aminomethyl)

The method for producing an aromatic aminomethyl of the present invention comprises hydrogenating an aromatic nitrile in a mixed solvent comprising a hydrocarbon solvent and a polar organic solvent having a solubility parameter (SP value) of 10 or more in the presence of a quaternary ammonium compound and a hydrogenation catalyst.

In the present production method, the order of blending a starting material, etc. is not particularly restricted, but it is preferable to introduce the hydrocarbon solvent, the polar organic solvent, the quaternary ammonium compound and the hydrogenation catalyst and then introduce hydrogen into a pressure container.

In order that a gas other than hydrogen, such as air, or water should not be introduced into the hydrogenation catalyst, the hydrogenation catalyst is preferably added as a slurry of the catalyst by immersing the catalyst in water and then replacing the water with the polar organic solvent.

For the reaction in the present production method, both of a batch process and a continuous process can be also carried out, but a batch process is preferable.

In the present invention, as hydrogen that is a starting material used in the hydrogenation, one having been purified does not need to be particularly used, and it may be an industrial-grade one. The hydrogen pressure in the reaction is preferably 2.0 to 20.0 MPa, more preferably 3.0 to 15.0 MPa, and still more preferably 5.0 to 10.0 MPa. When the hydrogen pressure is in the above range, the yield of a product is sufficient, a pressure container with high pressure becomes unnecessary, and the cost can be reduced, so that the above hydrogen pressure is preferable.

The reaction temperature is preferably 20 to 150° C., more preferably 50 to 130° C., and still more preferably 60 to 120° C. When the reaction temperature is in this range, a conversion ratio of the aromatic nitrile that is a starting material is good, and formation of a side product is inhibited, so that the yield is enhanced.

The reaction time varies depending on the reaction temperature, the hydrogen pressure, etc., but under the above conditions, the reaction time is usually set to 0.1 to 100 hours, and preferably 0.5 to 10 hours.

The resulting aromatic aminomethyl can be recovered using a known method. For example, the aromatic aminomethyl is preferably recovered by separating a gas component and a liquid component from a reaction mixture at the time of completion of the reaction, filtering out a solid component such as a catalyst, and then distilling the liquid component. It is also preferable to further distill the resulting aromatic aminomethyl to enhance purity.

EXAMPLES

The present invention will be specifically described based on the examples shown below, but the present invention is in no way restricted by these examples. In the following examples, a gas chromatograph was used for the composition analysis.

<Gas Chromatography (GC) Analysis Conditions>

The gas chromatography analysis was carried out under the following conditions.

Equipment used: Gas Chromatograph Nexis GC-2030 (manufactured by Shimadzu Corporation)

Column: DB-1 (length 30 m, inner diameter 0.53 mm, film thickness 1.5 μm)

Detector: FID ($H_2$ 30 mL/min, Air 300 mL/min)

Carrier gas: He (constant flow; average linear velocity 38 cm/sec)

Split ratio: 28.1

Injection port temperature: 300° C.

Detector temperature: 300° C.

Injection amount: 1.0 μL

Oven temperature: The temperature was raised from 50° C. up to 150° C. at 5° C./min, and after the temperature reached 150° C., the temperature was raised up to 280° C. at 10° C./min and then maintained for 7 minutes. Thereafter, the temperature was raised up to 300° C. at 10° C./min and maintained for 5 minutes.

<Conversion Ratio and Yield>

A conversion ratio of a starting material (terephthalonitrile) and a yield of a product (para-xylenediamine) were calculated from the amounts of the starting material and the product in a reaction mixture, which were measured by an internal standard method using the gas chromatography. In order to use diphenylmethane as an internal standard, a calibration curve was prepared in advance by using a solution of terephthalonitrile and para-xylenediamine of known concentrations.

A sample in which 0.5 g of diphenylmethane had been added to 5.0 g of a reaction mixture was prepared, the sample was subjected to gas chromatography measurement under the aforesaid conditions, and a conversion ratio and a yield were determined by the following equations.

Conversion ratio (mol %)=[1−(amount of terephthalonitrile in reaction mixture [mol])/(amount of terephthalonitrile in preparation[mol])]×100

Yield (mol %)=(amount of para-xylenediamine in reaction mixture [mol])/(amount of terephthalonitrile in preparation [mol])×100

<Reaction Time After Repeated Hydrogenation Reactions (Catalyst Deterioration Evaluation)>

Using a catalyst filtered out after hydrogenation reactions, the same operations as in Example 1 described later were carried out. A period of time from the time when the hydrogen pressure was set at 8.0 MPa after hydrogen purge to the time when hydrogen was no longer consumed was regarded as a reaction time after repeated hydrogenation reactions. The shorter the reaction time after repeated hydrogenation reactions is, the more deterioration of the catalyst is inhibited.

<Amount of Aluminum Dissolved After Repeated Hydrogenation Reactions (Catalyst Deterioration Evaluation)>

From a reaction mixture after completion of reaction, a sample for measuring an amount of aluminum dissolved was prepared by the following sample preparation procedure, and the amount of aluminum dissolved was measured by ICP atomic emission spectroscopy. Aluminum is contained in a Raney cobalt catalyst, and occurrence of deterioration of the catalyst can be seen by the dissolution of aluminum. On that account, the smaller the amount of aluminum dissolved is, the more deterioration of the catalyst is inhibited.

(Sample Preparation Procedure)

In a platinum crucible, 5.0 g of a reaction mixture was precisely weighed, and then the reaction mixture was heated to remove a solvent. Thereafter, ashing treatment was carried out at 600° C. for 3 hours. The resulting sample and the container were cooled, then 10 mL of a 12 mass % hydrochloric acid aqueous solution was added, and they were heated to dissolve the sample. The contents in the platinum crucible were transferred into a 25 mL volumetric flask and diluted to 25 mL with pure water, and then ICP spectroscopy was carried out.

<Preparation of Catalyst Slurry>

The following operations were carried out using a 50 mL beaker. In 30 mL of water, 5.90 g of a Raney cobalt catalyst (sponge cobalt catalyst) (RANEY 2724, manufactured by W.R. Grace & Co.) was introduced, and they were allowed to stand still to settle down the catalyst, followed by removing a supernatant by decantation. Next, 30 mL of methanol was added, stirring was carried out for 1 minute, and then a supernatant was removed in the same manner as above. The above replacement with methanol was carried out five times, thereby preparing a methanol slurry of the catalyst.

Example 1

(Production of Para-Xylenediamine)

In a 500 mL autoclave container, the methanol slurry of the catalyst (catalyst quantity 5.90 g) was introduced, and adjustment was made in such a manner that the total mass of methanol became 39.5 g. Subsequently, 51.8 g of terephthalonitrile, 197.3 g of m-xylene and 1.52 g of a 25% tetramethylammonium hydroxide aqueous solution (4.2 mmol, 0.38 g, as tetramethylammonium hydroxide) were introduced.

Nitrogen purge of the reactor was carried out by a method including pressurizing the reactor up to 0.5 MPa with nitrogen and returning the pressure to atmospheric pressure. This nitrogen purge was carried out three times in total, and then using hydrogen, hydrogen purge was carried out three times in total in the same manner as above.

The hydrogen pressure was set at 8.0 MPa, and the temperature was raised up to 100° C. while stirring at 1200 rpm, and reaction was carried out under the conditions of 8.0 MPa and 100° C. while feeding hydrogen. When hydrogen was no longer consumed, the reaction was completed. After completion of the reaction, a reaction mixture was cooled down to 50° C. and then subjected to pressure filtration at a pressure of 0.4 MPa to filter out the catalyst, thereby obtaining a reaction mixture containing para-xylenediamine that was a reaction product. The conversion ratio of terephthalonitrile was 100 mol %, and the yield of para-xylenediamine was 94.8 mol %.

Moreover, using the catalyst filtered out, the aforesaid hydrogenation reaction was carried out four times, that is, five times in total. The reaction time and the amount of aluminum dissolved in the fifth reaction are set forth in Table 2.

Examples 2 to 4

The same operations as in Example 1 were carried out to perform reaction, except that adjustment was made in such a manner that the total amount of methanol and m-xylene was the same as in Example 1 and the mass ratio of methanol to m-xylene was as shown in Table 1. The conversion ratio of terephthalonitrile and the yield of para-xylenediamine are set forth in Table 1.

Comparative Example 1

The same operations as in Example 1 were carried out to perform reaction, except that the amount of m-xylene was changed to 236.8 g and methanol was not used. Regarding the catalyst, a m-xylene slurry was used instead of the methanol slurry. The conversion ratio of terephthalonitrile and the yield of para-xylenediamine are set forth in Table 1.

Comparative Example 2

The same operations as in Example 1 were carried out to perform reaction, except that the amount of methanol was changed to 236.8 g and m-xylene was not used. The conversion ratio of terephthalonitrile and the yield of para-xylenediamine are set forth in Table 1.

TABLE 1

|  |  | Example 1 | Example 2 | Example 3 | Example 4 | Comparative Example 1 | Comparative Example 2 |
|---|---|---|---|---|---|---|---|
| Aromatic nitrile (starting material) | | Terephthalonitrile | Terephthalonitrile | Terephthalonitrile | Terephthalonitrile | Terephthalonitrile | Terephthalonitrile |
| Mixed solvent and composition | Hydrocarbon solvent | m-Xylene | m-Xylene | m-Xylene | m-Xylene | m-Xylene | — |
| | Polar organic solvent | Methanol | Methanol | Methanol | Methanol | — | Methanol |
| | Hydrocarbon solvent/polar organic solvent (mass ratio) | 83.3/16.7 | 90/10 | 80/20 | 60/40 | 100/0 | 0/100 |
| Quaternary ammonium compound | Quaternary ammonium compound | Tetramethylammonium hydroxide | Tetramethylammonium hydroxide | Tetramethylammonium hydroxide | Tetramethylammonium hydroxide | Tetramethylammonium hydroxide | Tetramethylammonium hydroxide |
| | Amount added (mmol) | 4.2 | 4.2 | 4.2 | 4.2 | 4 | 4 |
| Hydrogenation catalyst | | Raney cobalt | Raney cobalt | Raney cobalt | Raney cobalt | Raney cobalt | Raney cobalt |
| Aromatic aminomethyl (product) | | Para-xylenediamine | Para-xylenediamine | Para-xylenediamine | Para-xylenediamine | Para-xylenediamine | Para-xylenediamine |
| Evaluation of reaction mixture | Conversion ratio (mol %) | 100 | 100 | 100 | 100 | 100 | 100 |
| | Yield (mol %) | 94.8 | 92.9 | 91.6 | 86.0 | 79.6 | 64.4 |

Comparative Example 3

The same operations as in Example 1 were carried out to perform reaction, except that the tetramethylammonium hydroxide aqueous solution was not used. The conversion ratio of terephthalonitrile and the yield of para-xylenediamine are set forth in Table 2.

Comparative Examples 4 and 5

Using a basic compound shown in Table 2 instead of the tetramethylammonium hydroxide aqueous solution of Example 1, the same operations as in Example 1 were carried out to perform reaction. The conversion ratio of terephthalonitrile and the yield of para-xylenediamine are set forth in Table 2.

Comparative Example 6

Using sodium hydroxide instead of the tetramethylammonium hydroxide aqueous solution of Example 1, the same operations as in Example 1 were carried out to perform reaction. The conversion ratio of terephthalonitrile and the yield of para-xylenediamine are set forth in Table 2.

Moreover, using the catalyst filtered out, the aforesaid hydrogenation reaction was carried out twice, that is, three times in total. The reaction time and the amount of aluminum dissolved in the third reaction are set forth in Table 2.

Comparative Example 7

Using potassium t-butoxide instead of the tetramethylammonium hydroxide aqueous solution of Example 1, the same operations as in Example 1 were carried out to perform reaction. The conversion ratio of terephthalonitrile and the yield of para-xylenediamine are set forth in Table 2.

Moreover, using the catalyst filtered out, the aforesaid hydrogenation reaction was carried out four times, that is, five times in total. The reaction time in the fifth reaction is set forth in Table 2.

TABLE 2

|  |  | Example 1 | Comparative Example 3 | Comparative Example 4 | Comparative Example 5 | Comparative Example 6 | Comparative Example 7 |
|---|---|---|---|---|---|---|---|
| Aromatic nitrile (starting material) | | Terephthalonitrile | Terephthalonitrile | Terephthalonitrile | Terephthalonitrile | Terephthalonitrile | Terephthalonitrile |
| Mixed solvent and composition | Hydrocarbon solvent | m-Xylene | m-Xylene | m-Xylene | m-Xylene | m-Xylene | m-Xylene |
| | Polar organic solvent | Methanol | Methanol | Methanol | Methanol | Methanol | Methanol |
| | Hydrocarbon solvent/polar organic solvent (mass ratio) | 83.3/16.7 | 83.3/16.7 | 83.3/16.7 | 83.3/16.7 | 83.3/16.7 | 83.3/16.7 |
| Quaternary ammonium compound and basic compound | Quaternary ammonium compound | Tetramethylammonium hydroxide | — | — | — | — | — |
| | Other basic compounds | — | — | Triethylamine | Para-xylylenediamine | Sodium hydroxide | Potassium t-butoxide |
| | Amount added (mmol) | 4.2 | — | 4 | 2 | 4 | 4 |
| Hydrogenation catalyst | | Raney cobalt | Raney cobalt | Raney cobalt | Raney cobalt | Raney cobalt | Raney cobalt |
| Aromatic aminomethyl (product) | | Para-xylenediamine | Para-xylenediamine | Para-xylenediamine | Para-xylenediamine | Para-xylenediamine | Para-xylenediamine |

TABLE 2-continued

|  |  | Example 1 | Comparative Example 3 | Comparative Example 4 | Comparative Example 5 | Comparative Example 6 | Comparative Example 7 |
|---|---|---|---|---|---|---|---|
| Evaluation of reaction mixture | Conversion ratio (mol %) | 100 | 100 | 100 | 100 | 100 | 100 |
|  | Yield (mol %) | 94.8 | 50.6 | 54.4 | 55.2 | 95 | 90.3 |
| Evaluation of repeated hydrogenation reactions | Reaction time (hour(s), Xth time) | 1.5 (fifth time) | — | — | — | 1.9 (third time) | 2.5 (fifth time) |
|  | Amount of aluminum dissolved (ppm, Xth time) | 2.1 (fifth time) | — | — | — | 31.4 (third time) | — |

Example 5

Using a tetraethylammonium hydroxide aqueous solution instead of the tetramethylammonium hydroxide aqueous solution of Example 1, the same operations as in Example 1 were carried out to perform reaction. The conversion ratio of terephthalonitrile and the yield of para-xylenediamine are set forth in Table 3.

TABLE 3

|  |  | Example 1 | Example 5 |
|---|---|---|---|
| Aromatic nitrile (starting material) |  | Terephthalonitrile | Terephthalonitrile |
| Mixed solvent and composition | Hydrocarbon solvent | m-Xylene | m-Xylene |
|  | Polar organic solvent | Methanol | Methanol |
|  | Hydrocarbon solvent/ polar organic solvent (mass ratio) | 83.3/16.7 | 83.3/16.7 |
| Quaternary ammonium compound |  | Tetramethylammonium hydroxide | Tetraethylammonium hydroxide |
|  | Amount added (mmol) | 4.2 | 4.0 |
| Hydrogenation catalyst |  | Raney cobalt | Raney cobalt |
| Aromatic aminomethyl (product) |  | Para-xylenediamine | Para-xylenediamine |
| Evaluation of reaction mixture | Conversion ratio (mol %) | 100 | 100 |
|  | Yield (mol %) | 94.8 | 95.9 |

From the results of Tables 1 to 3, it has been found that when the production method of the examples is used, para-xylenethamine can be obtained in a high yield, and further, even when the reaction is repeatedly carried out, the catalyst is not deteriorated, and the reaction can be performed in a short time.

The invention claimed is:

1. A method for producing an aromatic aminomethyl, comprising:
   hydrogenating an aromatic nitrile in a mixed solvent comprising a hydrocarbon solvent and a polar organic solvent having a solubility parameter of 10 or more in the presence of a quaternary ammonium compound and a hydrogenation catalyst.

2. The method according to claim 1, wherein the quaternary ammonium compound is at least one selected from the group consisting of a tetraalkylammonium hydroxide and an organic acid tetraalkylammonium salt.

3. The method according to claim 1, wherein the mixed solvent has a mass ratio of the hydrocarbon solvent to the polar organic solvent of 60/40 to 99/1.

4. The method according to claim 1, wherein the mixed solvent comprises the hydrocarbon solvent and the polar organic solvent in a total amount of 90 to 100 mass %.

5. The method according to claim 1, wherein the hydrogenation catalyst comprises a metal catalyst comprising at least one selected from the group consisting of nickel and cobalt.

6. The method according to claim 1, wherein the quaternary ammonium compound is present in an amount of 1 to 20 mass % based on the hydrogenation catalyst.

7. The method according to claim 1, wherein the hydrocarbon solvent comprises an aromatic hydrocarbon solvent.

8. The method according to claim 1, wherein the polar organic solvent comprises an alcohol.

9. The method according to claim 1, wherein the mixed solvent does not comprise liquid ammonia.

10. The method according to claim 1, wherein in the mixed solvent comprises 5 mass % or less of water.

11. The method according to claim 1, wherein the aromatic nitrile comprises dicyanobenzene.

12. The method according to claim 1, wherein the aromatic nitrile comprises terephthalonitrile.

13. The method according to claim 1, wherein the aromatic aminomethyl comprises xylenediamine.

14. The method according to claim 2, wherein the mixed solvent has a mass ratio of the hydrocarbon solvent to the polar organic solvent of 60/40 to 99/1.

15. The method according to claim 2, wherein the quaternary ammonium compound is present in an amount of 1 to 20 mass % based on the hydrogenation catalyst.

16. The method according to claim 3, wherein the quaternary ammonium compound is present in an amount of 1 to 20 mass % based on the hydrogenation catalyst.

17. The method according to claim 7, wherein the polar organic solvent comprises an alcohol.

18. The method according to claim 14, wherein the quaternary ammonium compound is present in an amount of 1 to 20 mass % based on the hydrogenation catalyst.

19. The method according to claim 17, wherein the mixed solvent has a mass ratio of the hydrocarbon solvent to the polar organic solvent of 60/40 to 99/1.

20. The method according to claim 17, wherein the mixed solvent comprises the hydrocarbon solvent and the polar organic solvent in a total amount of 90 to 100 mass %.

* * * * *